United States Patent [19]

Pilato

[11] 4,225,679

[45] Sep. 30, 1980

[54] FLORAL FOAM PRODUCT AND METHOD OF PRODUCING THE SAME WHICH INCORPORATES A FLOWER PRESERVATIVE AND A BACTERIOCIDE

[75] Inventor: Louis A. Pilato, Bound Brook, N.J.

[73] Assignee: Pennock, Villamil and Pilato Inc., Bridgewater, N.J.

[21] Appl. No.: 42,794

[22] Filed: May 29, 1979

Related U.S. Application Data

[62] Division of Ser. No. 241, Jan. 2, 1979.

[51] Int. Cl.$^3$ .............................................. C08J 9/30
[52] U.S. Cl. ...................................... 521/109; 71/68; 521/124; 521/128; 521/181
[58] Field of Search ...................... 71/68; 521/181, 109

[56] References Cited

U.S. PATENT DOCUMENTS

| | | | |
|---|---|---|---|
| 2,753,277 | 7/1956 | Smithers | 71/68 |
| 3,049,444 | 8/1962 | Palombo | 428/357 |
| 3,287,104 | 11/1966 | Biggs | 71/68 |
| 3,697,457 | 10/1972 | Palombo | 521/53 |

FOREIGN PATENT DOCUMENTS

| | | | |
|---|---|---|---|
| 966680 | 4/1975 | Canada | 71/68 |
| 47-23369 | 6/1972 | Japan | 71/68 |

OTHER PUBLICATIONS

"The Greenhouse Environment" by J. W. Nastalerz, John Wiley & Sons (1977), pp. 573–580.

*Primary Examiner*—Morton Foelak
*Attorney, Agent, or Firm*—Zachary T. Wobensmith, 2nd; Zachary T. Wobensmith, III

[57] ABSTRACT

A foam product and method of producing the same for use in preserving cut flowers is provided which method provides in the manufacture of the product of foaming under mild conditions to preserve the wettability, and the preservative qualities of the foaming material and its additives so as to improve the life of the cut flowers which are mounted in the product.

5 Claims, No Drawings

FLORAL FOAM PRODUCT AND METHOD OF PRODUCING THE SAME WHICH INCORPORATES A FLOWER PRESERVATIVE AND A BACTERIOCIDE

This is a division of application Ser. No. 241, filed Jan. 2, 1979.

BACKGROUND OF THE INVENTION

1. Field of the Invention

This invention relates to a method of producing a foam product and a product of the type which is made into blocks and into which cut flowers are pushed for support, transport and storage and use.

2. Description of the Prior Art

The use of phenol-formaldehyde (PF) or urea-formaldehyde (UF) foamed products as supports for cut flowers have been in common usage in the floral industry for many years. Either of the described foam products requires vigorous acid catalyzed conditions to transform the PF or UF resin (with surfactant, wetting agent, blowing agent, and color) into foam which foam may vary in density from 1.0 to 2.0 lb./ft$^3$. A low density foam product is desirable for fragile flowers while a higher density foam product is suitable for heavy flowers or dry flowers. Foam properties desired are rapid wettability, good water retention, proper color, a crisp texture and ease of flower penetration, with good support and retention of the flower stems by the foam. The usual practice is to add a flower preservative to the water which the foams imbibes.

The U.S. Pat. to Smithers, No. 2,753,277 describes an absorbent material for floral arrangements wherein the foam is provided with a layer of wetting agent on the exterior to carry water into the interior of the foam mass. The foaming process is described as vigorous, and would deteriorate the flower preservative and bacteriocide.

The U.S. Pat. to Palombo, No. 3,049,444 discloses a foamed cellular synthetic material impregnated with a wetting agent and wherein the foam mass is provided with interior passages with a wetting agent disposed along the passages. The process has the same adverse affects as Smithers.

The U.S. Pat. to Jackson, Jr., No. 3,101,242 discloses a process of making flexible absorbent material wherein the foam mass prepared in accordance with Smithers U.S. Pat. No. 2,753,277 is compressed, bleached, leached to remove water soluble chemicals and treated with a wetting agent to increase its absorptive capacity.

The U.S. Pat. to Palombo, No. 3,697,457 describes a self wetting phenolic foam product wherein when making the foamed product, the wetting agents are mixed with the resin prior to foaming in seperate additions to obtain faster wetting and maximum water absorption in the foamed product.

The foaming condition as described for these prior art foam products including those disclosed by Smithers, the Palombo patents and Jackson are severe and decompose or char many flower preservatives, such as bacteriocides, sucrose, glucose and the like which would be incorporated into the resin prior to foaming.

The process for producing my foam product takes place under mild foaming conditions wherein sucrose, glucose and other sacchoridic materials as well as bacteriocides can be introduced into the resin prior to foaming. The foam appearance of the newly discovered composition in the absence of color additives exhibits no evidence of charring or decomposition of the preservative additive. The unusually mild foaming condition of my process, namely low concentration of acid catalyst, and longer curing time are beneficial in the preparation of a new floral foam composition with preservatives carried thereby. The desired product is described in "The Greenhouse Environment" by J. W. Mastalers, John Wiley & Sons (1977) at pp. 573-580.

SUMMARY OF THE INVENTION

A floral foam product and method of producing the same are disclosed which have incorporated therein and contains a flower preservative and a bacteriocide which is not adversely affected by the foaming process which produces the foamed product.

The principal object of the invention is to provide a foam product and method of making the product which product contains a flower preservative, bacteriocide and has high water retention.

It is a further object of the invention to provide a foam product and a method of producing the foam product that is simple and inexpensive.

Other objects and advantageous features of the invention will be apparent from the description and claims.

DESCRIPTION OF THE PREFERRED EMBODIMENT

In accordance with the invention, the method of producing the foamed product and the product can be accomplished by selecting a phenolic resin of low viscosity in the range of 1000 to 2000 CPS at ambient or room temperature which aids in dissolving the flower preservative as described below.

A flower preservative additive in the range of 1-10% with the preferred range of 2-5% is selected such as sucrose, glucose, fructose or other mono-, di- and trisaccharides which are water soluble or water dispersible.

A suitable bacteriocide is selected such as silver nitrate or acetate, 8-hydroxy quinoline nitrate or acetate, or sodium benzoate at a concentration of 10-200 PPM in an aqueous solution.

A preferred embodiment is given in the following example in which the quantities are stated in parts by weight.

| Resin Formulation Components | Composition |
|---|---|
| Phenolformaldehyde Resin GH 278 | 76-83 |
| Surfactant (Tween 40 or 60) (polyoxyethylene sorbitan monolaurate) | 3-4 |
| Wetting Agent (Texapon N-25) | 3-4 |
| Pentane (blowing agent) | 4-5 |
| Urea | 1 |
| Preservative, such as sucrose, glucose | 2-5 |
| Phenol Sulfonic Acid Catalyst | 4-5 |
| Bacteriocide, such as silver nitrate | 10-200 ppm |
| Color | 0.5 |

In preparing the foam product the phenolic resin, surfactant, wetting agent, urea (to reduce formaldehyde odor) preservative, bacteriocide and color are mixed at room temperature or 72° to 75° F. After a few minutes pentane is added to the mixture followed by the addition of the acid catalyst.

The resulting mixture is then poured into a mold which has been pre-heated to a temperature of 110° to 120° F. and allowed to sit for 30-60 minutes, the mold is placed into an oven and the foam expanded to its maximum height, at a temperature range of 110° to 120° F. The foam product is removed from the mold and cut into 9 inch×3.25 inch×4.25 inch size bricks for insertion of cut flowers.

While other suitable resins can be utilized the resin example given in the example is particularly suitable.

I claim:

1. The method of producing a foamed product of the type useful for floral displays which method comprises
    mixing at ambient temperature a phenol formaldehyde resin having a viscosity of 1000 to 2000 CPS with soluble additives comprising
        a surfactant,
        a wetting agent,
        a flower preservative selected from the group consisting of water soluble or dispersable saccharides, and
        a bacteriocide,
    adding a foaming agent to the mixture,
    then adding a catalyst to the mixture,
    delivering the aforesaid mixture into a preheated mold and retaining it in the mold for a period of about 30 to 60 minutes,
    heating the mold and its contents to foam the mixture in the mold for maximum foam formation, and
    removing the foamed material from the mold for use.

2. A method of producing a foamed product as defined in claim 1 in which
    said flower preservative is from the group consisting of sucrose, glucose, fructose, mono-saccharides, di-saccharides and tri-saccharides.

3. A method as defined in claim 1 in which said flower preservative is in the range of from 1 to 10% by weight.

4. A method of producing a foamed product as defined in claim 1 in which
    the bacteriocide is from the group consisting of silver nitrate, silver acetate, 8-hydroxy quinoline nitrate, 8-hydroxy quinoline acetate, and sodium benzoate.

5. A method as defined in claim 4 in which
    the bacteriocide is in the range of 10 to 200 ppm.

* * * * *

UNITED STATES PATENT AND TRADEMARK OFFICE
CERTIFICATE OF CORRECTION

PATENT NO. : 4,225,679
DATED : September 30, 1980
INVENTOR(S) : LOUIS A. PILATO

It is certified that error appears in the above—identified patent and that said Letters Patent is hereby corrected as shown below:

Column 2,

Line 49, after "Resin" cancel "GH" and insert - GB -

Signed and Sealed this

Sixteenth Day of December 1980

[SEAL]

Attest:

SIDNEY A. DIAMOND

Attesting Officer      Commissioner of Patents and Trademarks